United States Patent [19]
Cooper et al.

[11] Patent Number: 5,540,080
[45] Date of Patent: Jul. 30, 1996

[54] WIPER ASSEMBLY FOR OPTICAL SURFACES IN A CHILLED MIRROR HYGROMETER

[75] Inventors: Frank G. Cooper, South Huntington; David S. Russell, Mt. Sinai, both of N.Y.

[73] Assignee: Protimeter, Inc., Commack, N.Y.

[21] Appl. No.: 328,235

[22] Filed: Oct. 24, 1994

[51] Int. Cl.⁶ .................................................. G01N 19/10
[52] U.S. Cl. ..................... 73/29.02; 15/250.003; 15/250.15; 15/250.29
[58] Field of Search .............. 15/250.001, 250.003, 15/246, 250.15, 250.29; 359/507; 73/29.02, 335.01, 335.02, 335.06

[56] References Cited

U.S. PATENT DOCUMENTS 3,158,935  12/1964  Rosenthal ..................... 15/250.003
4,527,301  7/1985  Seitz ............................. 15/250.003
4,896,395  1/1990  Bissell .......................... 15/250.003

*Primary Examiner*—Mark Spisich
*Attorney, Agent, or Firm*—Michaelson & Wallace; Peter L. Michaelson, Esq.; Edward M. Fink, Esq.

[57] ABSTRACT

A wiper assembly for cleaning optical surfaces. The structure comprises a pneumatically activated wiper element including a wiping member connected to a spring member disposed within a cylinder. The wiper element is actuated by air pressure generated by a pumping element. The wiping member is connected to an end of a piston rod which passes longitudinally through the cylinder. When activated, the wiping element moves across an optical surface to be cleansed, and at a conclusion of its return stroke, has removed during its simple return stroke, frost, hydrocarbons, entrained particulate material and moisture from the optical surface.

16 Claims, 3 Drawing Sheets

WIPER ASSEMBLY FOR OPTICAL SURFACES IN A CHILLED MIRROR HYGROMETER

FIELD OF THE INVENTION

This invention relates to a novel means for cleaning optical surfaces. In particular, the present invention relates to a novel wiper assembly for cleaning mirrored surfaces employed in optical hygrometry.

BACKGROUND OF THE INVENTION

In recent years, humidity measurements have played an ever increasing role in industrial, laboratory and process control applications by enhancing the quality of products produced while simultaneously effecting significant economies.

The technology known as "chilled mirror hygrometry" was introduced some three decades ago and has resulted in the most accurate, stable and repeatable dewpoint measurement instruments to be sold commercially.

In this technology, there is typically employed an optically smooth surface which is continuously cooled by means of a thermoelectric cooling device to a temperature known as the dewpoint, the temperature at which a sample of air becomes saturated and produces dew or mist. This process involves the lowering of the temperature of the mirror at a precisely controlled rate until the formation of dew is detected. Before the dew so formed is able to form a continuous layer, the mirror is heated and the dew thereon evaporated. Accordingly, the mirror surface is essentially in a dry state and includes a dew layer for a very limited time period during which the dewpoint measurement is made.

Although this technology has been used successfully for many years, it has been recognized that any retention of a dew layer on a mirror surface tends to encourage airborne contaminants to adhere to the mirror. Such contamination impairs the reflective performance of the mirror, so resulting in the introduction of measurement errors unless a continuous cleansing procedure is employed. Heretofore, it has been common practice to effect this cleansing by wiping the optical surface with a smooth cloth such as a chamois or the like. Although such techniques have been used with a certain level of success, workers in the art have continued in their efforts to develop new techniques for reducing mirror contamination.

SUMMARY OF THE INVENTION

In accordance with the present invention, this end has been attained by the use of a novel wiper structure which can be automatically used to efficiently clean optical surfaces in one wiping stroke.

Briefly, the structure described is a pneumatically activated wiper element including a wiping means connected to a spring member disposed within a cylindrical shaft, the spring member being activated by gas pressure generated by a pumping means. When activated, the wiping element moves across the surface of the optical mirror, thereby removing in one stroke, frost, hydrocarbons, entrained particulate material and moisture. During the measurement process, the temperature is lowered at a precisely controlled rate until the formation of dew is detected by the hygrometer. Before the dew is able to form a continuous layer on the mirror, the mirror is heated and the dew on the mirror surface is evaporated. Accordingly, the mirror is almost always in the dry state and contains a layer of dew for only a short time at which point a dew measurement may be made. In a typical measurement process, the mirror is cycled in three steps. The first step involves cooling of the mirror from a level above ambient temperature to cross the dewpoint, thereby allowing dew to form in a uniform and repeatable manner so that correct formation of dew is detected. In the next stage, following completion of dew detection the current to the cooling device is reversed, so causing the mirror to rise in temperature to a few degrees above ambient temperature. The final stage represents a short period of time between successive cooling stages which allows the mirror to stabilize. In this processing sequence, the dew is present on the mirror surface for a short period of time. However, it is during this period that contaminant buildup occurs which necessitates the type of cleansing procedure described herein.

BRIEF DESCRIPTION OF THE DRAWINGS

The invention will be more readily understood by reference to the following detailed description taken in conjunction with the accompanying drawings wherein.

In order to facilitate understanding, identical reference numerals have been used to denote identical elements common to the figures.

DETAILED DESCRIPTION OF THE INVENTION

Figure 1:
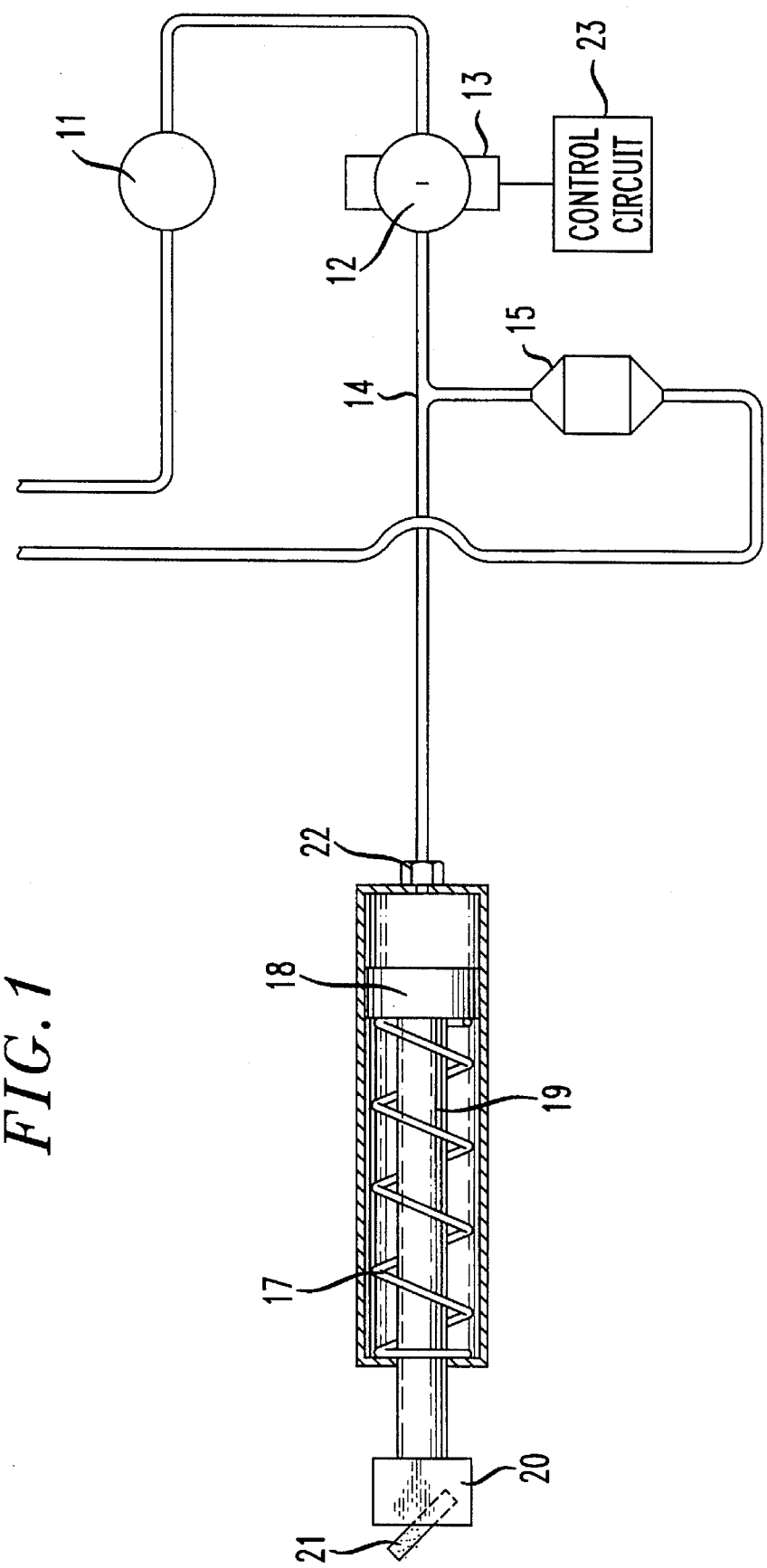
FIG. 1 is a schematic representation of the pneumatic elements of the wiper assembly of the invention and the associated apparatus employed in conjunction with its use.

With reference now more particularly to FIG. 1, there is shown a schematic representation of the pneumatic elements of the wiper assembly of the invention in cooperative relationship with associated members of the hygrometry operation. Shown is an air chamber 11 connected to pump means 12 which is operated by applying a bias thereto via conventional circuit 13. Pump 12 is connected via conduit 14 to an orifice 15 (typically 0.0012" in diameter) which permits bleed out of air pressure so that the pump can draw a constant flow of process gas, typically though not exclusively air, through cylinder 16 without actuating piston 18. Pump 12 is also connected to the pneumatic cylinder by conduit 14. Assembly 16 comprises a pneumatic cylinder having disposed therein a spring member 17 connected to piston 18 which, itself, is connected by means of hexagonal shaft or piston rod 19 which runs through the cylinder and is connected at the other end thereof, typically through a threaded connection, to a rectangular blade holder 20. The holder has an angular opening for insertion of a hard rubber blade 21 therein which is used to effect wiping of a mirror assembly. The conduit 14 is affixed to cylinder 16 by means of hexagonal nut 22.

In the operation of the wiper assembly, pump 12 is initially operated at approximately one-sixth of its capacity with a relatively small amount of process gas being pumped therethrough. When it is desired to operate the wiper assembly, increased drive power is applied to pump 12, through circuit 13, by means of control electronics 23 to increase the pressure produced by the pump, thereby increasing the pressure of the process gas which is pumped to assembly 16 to a pressure of approximately 10 psi. At that juncture, piston 18 drives piston rod 19 to impinge upon spring 17 and so compress it, so causing piston rod 19 to distend laterally from cylinder 16 in a horizontal direction, by pneumatic force, across the surface of an optical mirror. After moisture is formed upon the surface of the mirror, the piston is retracted by a return force exerted by the spring and by reducing the pressure applied thereto, through actively reducing current to pump 12 by control electronics 23, and the wiper assembly mechanically wipes away the contaminants such as moisture, hydrocarbons and the like from the mirror. Thus, in one stroke the mirror surface is wiped and the wiper withdrawn. The period at which the wiper is operated is controlled in a conventional manner through the control electronics.

Studies have revealed that it is necessary to effect wiping of the surface of typical mirrors employed in hygrometry operations no more frequently than once each week. Clearly, this enhances the wiping operation, by reducing its periodicity and thus effecting substantial operational economies to the point where wiping using our inventive system can be essentially maintenance-free. Additionally, it has been noted that the wiper blade does not wear out.

Figure 2:
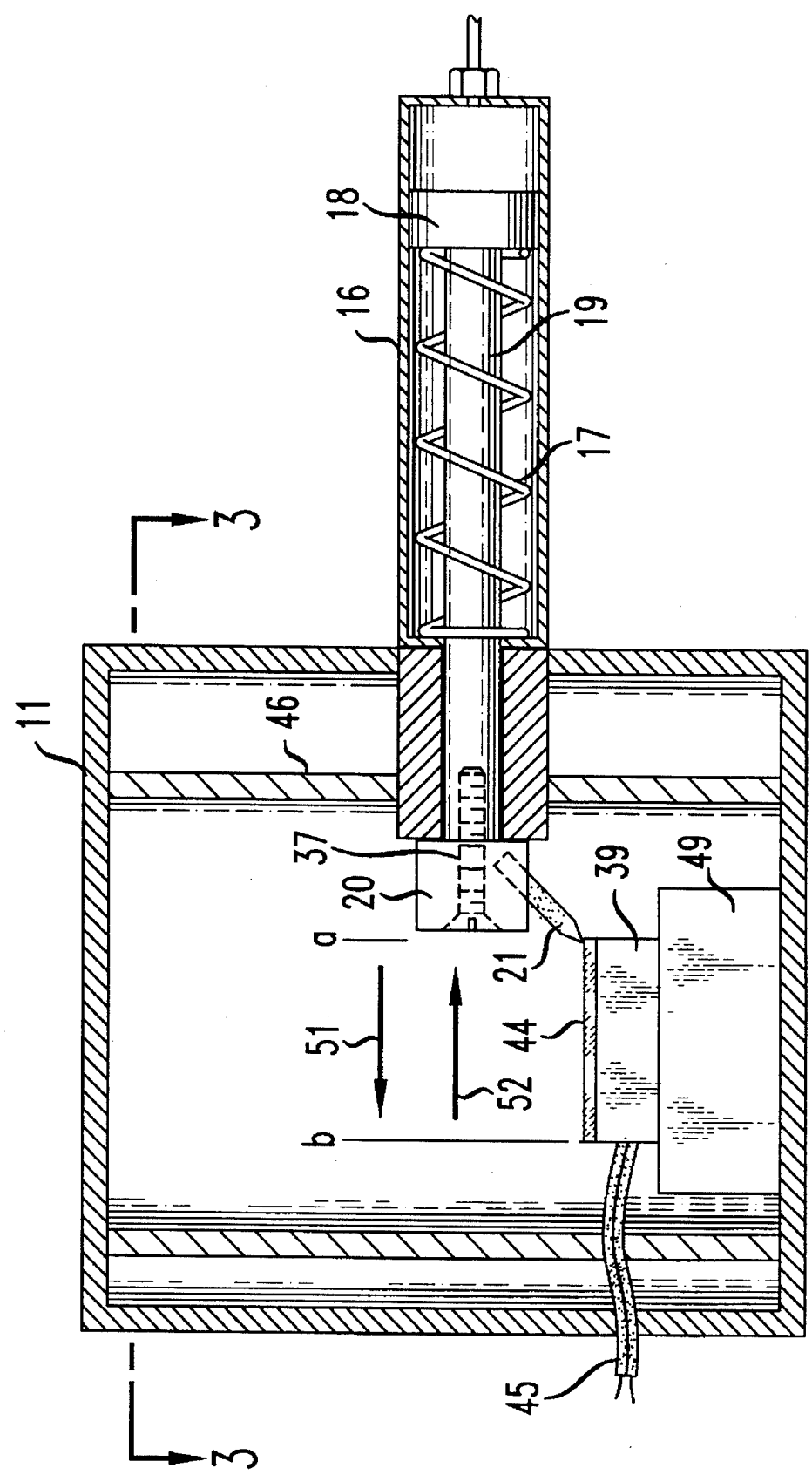
FIG. 2 is a simplified side elevational view, in cross-section, of the wiper assembly of the invention and taken along lines 2—2 shown in FIG. 3.
Figure 3:
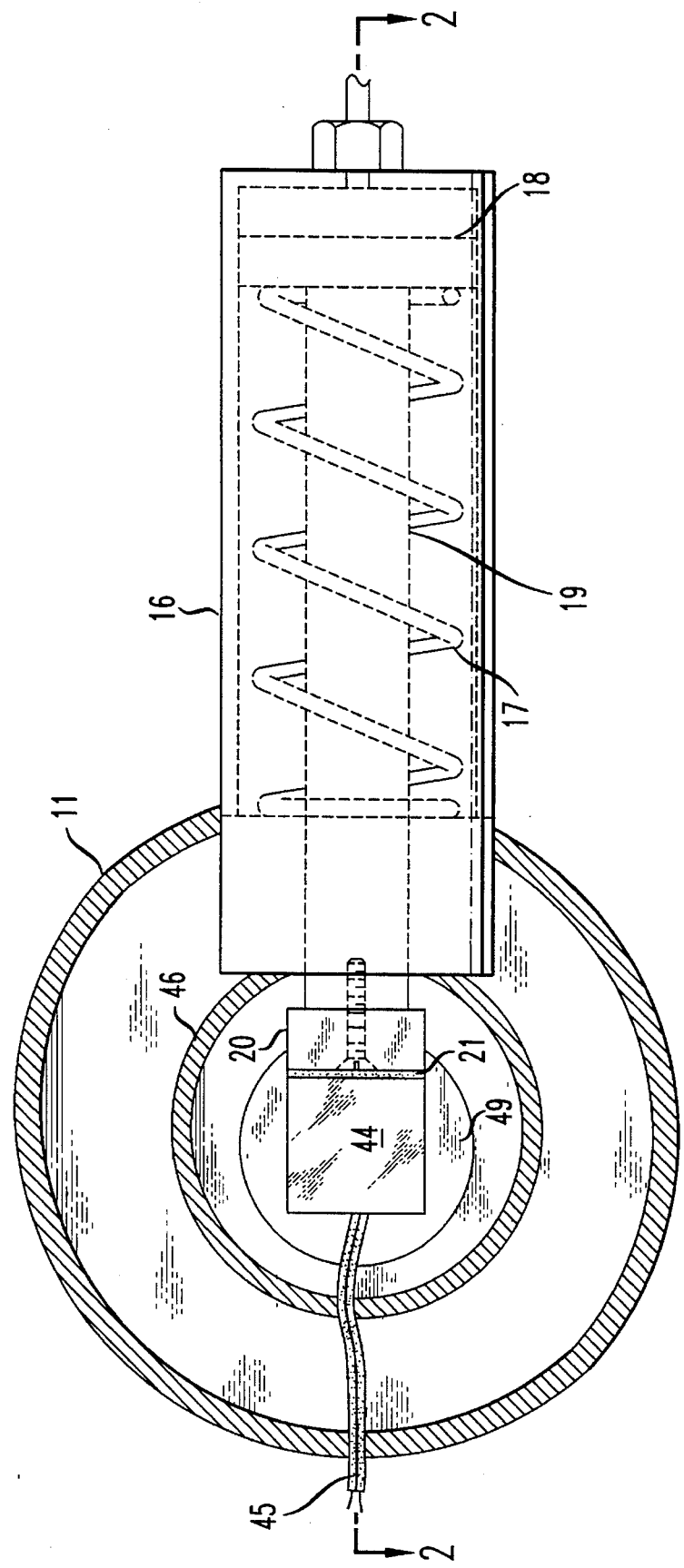
FIG. 3 is a simplified top view in cross-section of the wiper assembly of the invention shown in FIG. 2 and taken along lines 3—3 therein.

With reference now to FIG. 2, there is shown a simplified cross-sectional view of the wiper assembly of the invention and taken along line 2—2 shown in FIG. 3. Shown in FIG. 2 is pneumatic cylinder 16 having disposed therein piston rod 19 connected to piston 18 which extends through and abuts spring member 17. Piston rod 19 extends through a head of cylinder 16 and engages wiper head 20. This head contains a wiper blade 21 positioned at approximately a 45 degree angle to the horizontal. The wiper head is secured to piston rod 19 by means of a threaded screw 37. The cylinder suitably threads into the air chamber 11. The wiper assembly described herein is appropriately positioned partially extending into air chamber 11. When piston rod 19 fully extends, the wiper blade 21 moves, in a direction shown by arrow 51, to position b, normal to the surface of an optical, mirror 44, and in contact with a left edge of a top surface of the mirror. This mirror is disposed upon a Peltier thermoelectric heat pump 39, which itself is mounted to support 49 and which has electrical wiring 45 emanating therefrom. When retracted, the wiper blade returns, in a direction shown by arrow 52, to position a, again normal to the surface of mirror 44, but now in contact with a right edge of the top surface of the mirror (as shown). Air chamber 11 is typically metallic, such as, e.g., an aluminum alloy, and, except for appropriate inlet and outlet pneumatic ports (not shown for simplicity), is sealed.

The wiper blade selected for use in the described structure may be selected from among any of the well known materials in the rubber family commonly used for this purpose. A preferred embodiment involves the use of a hard rubber blade, typically available through known commercial sources.

With reference now to FIG. 3, there is shown a top view in cross-section of the wiper assembly of the invention taken along line 3—3 shown in FIG. 2. Shown is pneumatic cylinder 16 including wiper assembly 20 partially extending into air chamber 11 within which an optical mirror 44 is positioned for detection of humidity. Mirror 44 is positioned upon a Peltier thermoelectric heat pump (shown in FIG. 2) which is connected by means of wiring 45 to a controlled source of current (not shown). Within chamber 11 and disposed essentially concentric to the optical mirror is conventional porous (40 micron) filter 46 which is designed to prevent most particulate contaminants from reaching the surface of mirror 44.

While the invention has been described in detail in the foregoing description, it will be understood by those skilled in the art that variations may be made without departing from the spirit and scope of the invention. Thus, for example, the material employed in construction of the wiper assembly may be varied as may the composition of the wiper blade.

What is claimed is:

1. Apparatus for a chilled mirror hygrometer for measuring dewpoint comprising:

an air chamber for receiving a gaseous atmosphere; a mirror situated within the chamber and having a rectangular cross-section with first and second opposing surfaces, with the first surface having first and second opposing sides, the first surface of the mirror being exposed to the atmosphere within the chamber and the second surface of the mirror being in abutting thermal communicative contact with an upper surface of a thermo-electric heat pump assembly;

the thermo-electric heat pump assembly fixedly secured to an internal surface of the air chamber, wherein electrical current is controllably supplied to the heat pump assembly to selectively vary a temperature of the first surface of the mirror from a temperature above which condensation from the atmosphere forms on the first surface to a temperature below which the condensation forms, the temperature at which the condensation forms being the dewpoint; and a wiper assembly a portion thereof which is fixedly secured with respect to the mirror and having a cleaning element that controllably slides along the first surface of the mirror;

a drive assembly, connected to the wiper assembly, so as to control sliding movement of the cleaning element along the first surface such that, to clean the first surface, the cleaning element is moved from an initial position to an extended position prior to the formation of the condensation and then moved back to the initial position after the condensation has formed such that the condensation on the first surface cooperatively with a wiping action of the cleaning element against the first surface mechanically washes contaminants off the first surface of the mirror.

2. The apparatus in claim 1 wherein the wiper assembly comprises:

a head having a wiper blade, the wiper blade being situated at a predefined angle to the first surface of the mirror and oriented such that a lower edge of the blade rests on and transversely extends across the first surface; and an actuator, connected to the air chamber and the head, for controllably moving said head across said first surface such that the wiper blade slidably traverses across the first surface between the initial and the extended positions, the initial and extended positions being located in a vicinity of the first and second sides, respectively.

3. The apparatus in claim 2 wherein the drive assembly comprises a means for operating the actuator so as to periodically move the wiper blade across the first surface between the initial and extended positions so as to clean the mirror.

4. The apparatus on claim 3 wherein the predefined angle is substantially 45 degrees with respect to the first surface of the mirror.

5. The apparatus in claim 3 wherein the wiper blade is formed of rubber.

6. The apparatus on claim 5 wherein the predefined angle is substantially 45 degrees with respect to the first surface of the mirror.

7. The apparatus in claim 3 wherein the actuator comprises:

a pneumatic cylinder having a piston and a piston rod, the rod having distal and proximal ends, with the piston being situated at the proximal end and the distal end being connected to the head; and a return spring concentrically located around the piston rod and within the cylinder such that upon pressurization of the cylinder to a predefined pressure sufficient to distend the piston rod, the spring is compressed and upon sufficient de-pressurization of the cylinder, a return force provided by the spring retracts the piston rod back into the cylinder.

8. The apparatus in claim 7 wherein the actuator operating means comprises:

a pneumatic pump, connected to the cylinder, for varying the pressurization of the cylinder; and means, connected to the pump, for controllably operating the pump to increase the pressurization of the cylinder prior to the formation of the condensation so as to move the wiper blade from the initial position to the extended position and then, after the condensation has formed, reducing the pressure so as to retract the wiper blade back to the initial position so as to form a cycle of wiper movement.

9. The apparatus on claim 8 wherein the predefined angle is substantially 45 degrees with respect to the first surface of the mirror.

10. The apparatus in claim 8 wherein the wiper blade is formed of rubber.

11. The apparatus in claim 3 wherein the heat pump assembly comprises:

a Peltier thermo-electric heat pump having upper and lower surfaces, the upper surface of which lies in abutting thermal communicative contact along its length with the second surface of the mirror; and a support having upper and lower surfaces, the lower surface of the heat pump being fixedly connected to the upper surface of the support and the lower surface of the support being fixedly connected to the internal surface of the air chamber; and where in the Peltier heat pump and support are aligned with each other.

12. The apparatus in claim 11 wherein the actuator operating means comprises:

a pneumatic pump, connected to a cylinder, for varying the pressurization of the cylinder; and means, connected to the pump, for controllably operating the pump to increase the pressurization of the cylinder prior to the formation of the condensation so as to move the wiper blade from the initial position to the extended position and then, after the condensation has formed, reducing the pressure so as to retract the wiper blade back to the initial position so as to form a cycle of wiper movement.

13. The apparatus on claim 12 wherein the predefined angle is substantially 45 degrees with respect to the first surface of the mirror.

14. The apparatus in claim 12 wherein the wiper blade is formed of rubber.

15. The apparatus in claim 12 wherein the air chamber is cylindrically shaped and the heat pump assembly is situated on an internal floor thereof.

16. The apparatus in claim 15 wherein the air chamber further comprises a cylindrically shaped filter which substantially extends through a height of the chamber and encircles the heat pump assembly so as to prevent particulate contaminants of a predefined size present in the atmosphere from reaching the first surface of the mirror.

* * * * *